(12) United States Patent
Cooper et al.

(10) Patent No.: US 7,736,663 B2
(45) Date of Patent: Jun. 15, 2010

(54) COSMETIC AND PERSONAL CARE COMPOSITIONS

(75) Inventors: Julie Hutchison Cooper, Wirral (GB); Michael Douglas Eason, Wirral (GB); Ezat Khoshdel, Wirral (GB); Brodyck James Royles, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 1824 days.

(21) Appl. No.: 10/493,083

(22) PCT Filed: Sep. 12, 2002

(86) PCT No.: PCT/EP02/10273

§ 371 (c)(1), (2), (4) Date: Apr. 16, 2004

(87) PCT Pub. No.: WO03/032929

PCT Pub. Date: Apr. 24, 2003

(65) Prior Publication Data

US 2005/0031566 A1  Feb. 10, 2005

(30) Foreign Application Priority Data

Oct. 17, 2001 (GB) ................ 0124967.1

(51) Int. Cl.
*A61K 8/58* (2006.01)
*A61K 8/89* (2006.01)
*C07C 63/307* (2006.01)
*C07C 69/76* (2006.01)
*C07C 233/65* (2006.01)

(52) U.S. Cl. ............... 424/401; 424/70.12; 528/10

(58) Field of Classification Search .............. None
See application file for complete search history.

(56) References Cited

U.S. PATENT DOCUMENTS

| 3,130,220 | A |   | 4/1964  | Van Strien et al. |
|-----------|---|---|---------|-------------------|
| 4,659,573 | A | * | 4/1987  | Frischling et al. ............. 424/63 |
| 5,776,444 | A | * | 7/1998  | Birtwistle et al. ........ 424/70.12 |
| 5,882,635 | A | * | 3/1999  | Ramin et al. ................... 424/61 |
| 6,166,093 | A | * | 12/2000 | Mougin et al. ............ 514/772.1 |
| 6,320,018 | B1 | * | 11/2001 | Sijbesma et al. ............ 528/310 |

FOREIGN PATENT DOCUMENTS

| EP | 0180149 A2 | 5/1986 |
| EP | 0 640 643 A2 | 3/1995 |
| EP | 0 930 290 A1 | 7/1999 |
| GB | 1 390 715 | 4/1975 |
| WO | 97/36572 A1 | 10/1997 |
| WO | 98/14504 | 4/1998 |
| WO | 02/098377 A1 | 10/2002 |

OTHER PUBLICATIONS

L.R. Rieth et al., "Polymerization of Ureidopyrimidinone-Functionalized Olefins by Using Late-Transition Metal Ziegler-Natta Catalysts: Synthesis of Thermoplastic Elastomeric Polyolefins" Angew. Chem. Int. Ed., 2001, 40(11), pp. 2153-2156.*
International Search Report Application No. PCT/EP 02/10273 mailed Apr. 23, 2003.
Database WPI, Thomson Derwent, Class A25, WPI Acc No.: 1977-45847Y/197726; JP 52 059700A (Mitsubishi Electric Corp.), May 17, 1977, Abstract.
Database WPI, Thomson Derwent, Class A60, WPI Acc No. 1977-38861Y/1997722: JP 52 049297A (Mitsubishi Electric Corp), Apr. 20, 1977, Abstract.
Database WPI, Thomson Derwent, Class A41, WP Acc No: 1978-61386A/197834; JP 53 082743A (Okura Ind. Co., Ltd.), Jul. 21, 1978, Abstract.
Database WPI, Thomson Derwent, Class A25, WPI Acc No. 1990-324563/199043; JP 2232226A (Taki Chemical KK), Sep. 14, 1990, Abstract.
Database WPI, Thomson Derwent, Class A41, WPI Acc No. 1977-444072/188741; JP 92 02758A (Mitsui Toatsu Chem. Inc.), Aug. 5, 1997, Abstract.

* cited by examiner

*Primary Examiner*—Frederick Krass
*Assistant Examiner*—Brian Gulledge
(74) *Attorney, Agent, or Firm*—Karen E. Klumas

(57) ABSTRACT

Hair treatment compositions comprise: at least one polymer comprising at least two hydrogen-bonding moieties, which may be the same or different, covalently bonded to each other by at least one polymeric, oligomeric or monomeric linker, each moiety having at least 3 groups capable of forming a hydrogen bond with the same moiety or a different moiety; and from 0.1 to 50% by weight of the total composition of a hair conditioning agent and/or a cosmetically acceptable surfactant.

9 Claims, No Drawings

COSMETIC AND PERSONAL CARE COMPOSITIONS

This invention relates to cosmetic and personal care composition containing one or more polymers, to a method of treating hair with the polymers and to the use of the polymers for the cosmetic treatment of hair.

The desire to have the hair retain a particular shape or style is widely held. The most common approach for accomplishing styling of hair is the application of a composition to dampened hair, after shampooing and/or conditioning, or to dry, styled hair. These compositions provide temporary styling benefits and can readily be removed by water or shampooing. To date, the materials employed in hair care compositions to provide styling benefits have generally been natural or synthetic resins and have been applied in the form of, for example, sprays, mousses, gels and lotions.

Recently, it has become desirable to have a high level of style retention, or strong hold, delivered from a hair spray composition. In a typical hair spray, hold is achieved by the use of commercially available styling polymers, such as AMPHOMER™, supplied by National Starch Chemical Company, LUVIMER™, supplied by BASF, GANTREZ™, supplied by ISP Chemicals and also silicone graft copolymers, supplied by Mitsubishi Chemicals.

Typically, the styling polymers have a carbon backbone comprising various hydrophilic and hydrophobic vinylic monomers. These polymers can be non-ionic or they can carry a charge, usually a negative charge. The hydrophilic monomer is employed to render the polymer water-soluble and the hydrophobic monomer is generally selected to enhance humidity resistance of the styling resins.

There remains a need for further cosmetic and personal care compositions that provide acceptable hair styling benefits without accompanying sensory negatives.

The design and construction of the so called self-assembling supramolecular polymers, which can be defined as arrays of small molecules held together by secondary forces, has been described, for example, in J. M. Lehn, *Angew. Chem., Int. Ed. Eng.,* 1990, 29, 1304, C. M. Paleos and D. Tsiourvas, *Angew. Chem., Int. Ed. Eng.,* 1995, 34, 1696 and N. Zimmerman, J. S. Moore, and S. C. Zimmerman, *Chem. Ind.,* 1998, 604. One approach is the exploitation of specific hydrogen bonding molecules. Most systems are based on AA (or $A_2$) type monomers or components (hydrogen bonding acceptors) plus BB (or $B_2$) type monomers (hydrogen bonding donors) or AA+BB type (or $A_2+B_2$) complimentary pairs. Several examples of components or building blocks that could be used in this way to produce such architectures have been described.

Sijbesma et al (Science, 1997, 278, pp 1601-1604) teaches a reversible self-assembling polymer system in chloroform as solvent. The system comprises two linked 2-ureido-4-pyrimidone units. The 2-ureido-4-pyrimidone units can dimerise via a self-complementary array of four co-operative hydrogen bonds. Sijbesma et al suggests that polymer networks with thermodynamically controlled architectures can be formed for use in coatings and hot melts.

Hirschberg et al (Nature, 2000, 407, pp 167-170) describes bifunctionalised ureidotriazone units, optionally connected by a spacer, carrying solublising chains at the periphery. Through dimerisation via self-complementary quadruple hydrogen bonding and solvophobic interactions, the ureidotriazone units connected by a spacer assemble into supramolecular random coil polymers in chloroform and helical columns in dodecane as solvent.

Clearly, neither Sijbesma et al nor Hirschberg et al contemplates the use of hydrogen bonding polymers in cosmetic compositions for personal use.

WO 97/36572 discloses deodorant compositions which are thickened with siloxane-urea copolymers. Organopolysiloxanes which generate intramolecular or intermolecular cross-linking are disclosed as hair setting agents in EP 0 640 643.

According to the present invention, there is provided a hair treatment composition comprising: at least one polymer comprising at least two hydrogen-bonding moieties, which may be the same or different, covalently bonded to each other by at least one polymeric, oligomeric or monomeric linker, each moiety having at least 3 groups capable of forming a hydrogen bond with the same moiety or a different moiety; and from 0.1 to 50% by weight of the total composition of a hair conditioning agent and/or a cosmetically acceptable surfactant.

In a further aspect, the invention provides the use of a polymer of the composition of the first aspect of the invention in a cosmetic or personal care composition.

In another aspect, the invention provides a method of treating hair comprising applying to the hair at least one polymer of the composition of the first aspect of the invention.

In yet another aspect, the invention provides the use of a polymer of the composition of the first aspect of the invention in the cosmetic treatment of hair.

A further aspect of the invention relates to a compound having the following structure:

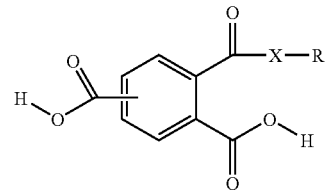

Where X is oxygen or an amide (NH) group and R is either a covalent linking unit, linking the hydrogen-bonding moiety to a polymeric, oligomeric or monomeric linker, or a side group selected from H, $C_1$-$C_{24}$ alkyl, $C_{2-24}$ alkenyl, $C_{2-24}$ alkynyl, aryl, aralkyl or heteroaryl groups optionally substituted, or polyoxyethylene or polyoxypropylene or a random or block copolymer thereof.

A method of preparing the compound above is also described. The method comprises selecting a polymer having at least two amino or hydroxy groups or mixtures thereof and reacting the polymer with trimellitic anhydride.

The personal care compositions according to the present invention include at least one polymer comprising at least two hydrogen-bonding moieties, which may be the same or different, covalently bonded to each other by at least one polymeric, oligomeric or monomeric linker, each moiety having at least 3 groups capable of forming a hydrogen bond with the same or different moieties.

Cosmetic and personal care compositions of the invention, particularly hair styling compositions, comprise at least one polymer which is capable of hydrogen bonding either wholly or partially to itself and/or wholly or partially to other, for example polymeric, molecules including, for example, natural or synthetic hair fibres, in order to provide improved hold, for example.

The at least one polymer preferably comprises at least two hydrogen-bonding moieties which may be the same or different, each hydrogen-bonding moiety having at least 3, preferably at least 4, groups capable of forming a hydrogen bond with the same or different moieties.

Each hydrogen-bonding moiety may have hydrogen-bonding donor and/or acceptor groups. Preferably each hydrogen-bonding moiety has both donor and acceptor groups. However, it is possible for hydrogen-bonding moieties to have only donor or acceptor groups. Thus, for example, a polymer having hydrogen-bonding moieties with solely donor groups may be used together with a polymer having hydrogen-bonding moieties with solely acceptor groups. Also, for instance, one polymer may comprise both hydrogen-bonding moieties which are wholly donor groups and hydrogen-bonding moieties which are wholly acceptor groups.

Preferred polymers additionally have some monomeric units having only one hydrogen bonding group. Such monofunctional monomers are present as chain stoppers and can be used to control the molecular weight of the polymer. It is preferable if these mono-functional monomers are present at 10% or less of the total number of monomeric material comprising the polymer, more preferably less than 5%.

The polymers according to the present invention are also referred to as "hydrogen-bonding polymers" in order to distinguish them, where necessary, from other polymers which may be present in the compositions or methods of the invention.

The hydrogen-bonding moiety comprising at least 3 hydrogen bonding groups preferably has the same structure as the corresponding moiety with which it forms hydrogen bonds when the moiety contains an even number of hydrogen bonding groups. When the hydrogen-bonding moiety contains an odd number of hydrogen bonding groups, the corresponding moiety with which it bonds must be complementary. This is particularly preferred when the hydrogen-bonding polymer forms hydrogen bonds to other hydrogen-bonding polymers, whether in an intramolecular or intermolecular fashion. However, the hydrogen-bonding polymer of the present invention may also be capable of forming hydrogen bonds to polymers such as, for example, keratin or other polymers or monomers that occur, for example, in natural or synthetic hair. In such cases, the corresponding moiety with which the hydrogen-bonding moiety forms hydrogen bonds is suitably the same or different but preferably different. Preferably, the hydrogen-bonding polymer is capable of forming at least six, more preferably at least eight, hydrogen bonds to other polymers and monomers.

The one or more polymers may bond to each other substantially only as a result of hydrogen-bonding interactions. However, other non-covalent forces may also contribute to the bonding such as, for example, electrostatic forces, van der Waal's forces and, when the hydrogen-bonding moieties comprise one or more aromatic rings, pi-pi stacking.

The strength of each hydrogen bond preferably varies from 1-40 kcal/mol, depending on the nature and functionality of the donor and acceptors involved.

Thus, suitable compositions may comprise a single hydrogen-bonding polymer according to the present invention or mixtures of, for example, 2 or more hydrogen bonding polymers according to the present invention. Suitable mixtures for use in the compositions of the present invention preferably comprise from 2 to 5 different polymers. More preferably, suitable mixtures for use in compositions according to the present invention comprise two different hydrogen-bonding polymers.

Also preferred are mixtures of hydrogen-bonding polymers comprising two hydrogen-bonding moieties with hydrogen-bonding polymers comprising more than two hydrogen-bonding moieties (eg, from 3 to 10 hydrogen-bonding moieties, such as 3 hydrogen-bonding moieties). Such mixtures can provide varying degrees of cross-linking interactions between the polymers and this can be used to tailor the properties of the composition. The polymers in the mixture are preferably compatible and compatibility can be determined readily by those skilled in the art.

In one embodiment of the invention, however, only one hydrogen-bonding polymer according to the present invention is present in the compositions.

The at least one polymer according to the invention suitably comprises from 2 to 100 hydrogen-bonding moieties, preferably from 2 to 20, more preferably from 2 to 10 hydrogen-bonding moieties. For example, the at least one polymer may comprise 2, 3, 4, 5, 6, 7, 8, 9 or 10 hydrogen-bonding moieties. It is particularly preferred if the hydrogen-bonding polymer according to the invention comprises 2 hydrogen-bonding moieties.

Polymers of the invention may be linear, branched or hyperbranched. Hydrogen-bonding moieties may suitably be present at the two or more ends of the polymer chain and/or along the one or more backbones of the polymer.

The hydrogen-bonding moieties according to the present invention suitably comprise less than ten, preferably less than five, repeat units of the same or different building blocks, or monomers, in a linear sequence. It is particularly preferred if the hydrogen-bonding moieties comprise one building block. As used herein the term "building block" refers to any molecular unit that is not in itself a polymer. The building block is also suitably a functionalised molecule that comprises in addition to carbon and hydrogen at least three heteroatoms selected from the group consisting of nitrogen, oxygen, sulfur, phosphorus and fluorine and mixtures thereof.

The at least two hydrogen-bonding moieties are suitably the same or different and comprise at least one building block which is the same or different. Preferably, however, the hydrogen-bonding polymer comprises hydrogen-bonding moieties that are all the same, in that they comprise the same building block.

Suitable hydrogen-bonding moieties for the purposes of the present invention are those having at least three, preferably at least four, groups which are capable of forming a hydrogen bond with the same or different moieties. It is particularly preferred that the hydrogen-bonding moieties have four groups that are capable of forming a hydrogen bond with the same or different moieties.

The groups in the hydrogen-bonding moieties which are capable of forming a hydrogen bond with the same or different moieties may suitably be selected from, for example, >C=O, —COO—, —COOH, —O—, —O—H, —NH$_2$, >N—H, >N—, —CONH—, —F, —C=N— groups and mixtures thereof.

Preferably the groups are selected from >C=O, —O—H, —NH$_2$, >NH, —CONH—, —C=N— and mixtures thereof.

Particularly suitable examples of hydrogen-bonding moieties include heterocycles and derivatives thereof, such as, for example, derivatives of pyrimidone and triazine, comprising at least three groups that are capable of forming a hydrogen bond to the same or different moieties. It is sometimes possible in the case of, for example, heterocyclic compounds for two or more structurally distinct compounds to exist in rapid equilibrium ie, for tautomers to be present, usually through the shift of a proton. The amount of each tautomer present will be determined, amongst other factors, by relative stability. All, some or none of the tautomeric forms of a particular heterocycle may be suitable candidates for hydrogen-bonding moieties according to the present invention. However, the tautomers of a heterocycle are considered to fall within the scope of the present invention only when they are capable of satisfying the requirement of having at least three groups capable of forming a hydrogen bond with the same or different moieties.

Other suitable hydrogen-bonding moieties include short peptides comprising one, two or three peptide bonds. For example, the hydrogen-bonding moieties may have the formula -(A1)(A2)(A3)(A4)-Q, wherein A1, A2, A3 and A4 are the same or different amino acid residues and Q is OH, $NH_2$ or a derivative thereof (eg, derivatised by alkylation or acylation of either O or N). Amino acid residues may be derived from natural amino acids (eg, arginine) or synthetic amino acids.

Hydrogen bonds are relatively weak, non-covalent interactions usually formed between an electronegative atom, such as, for example, oxygen, where the oxygen atom may either be covalently bound to another usually less electronegative atom, such as, for example, carbon, by a single or a double covalent bond, or a nitrogen atom either covalently bound to another usually less electronegative atom by a single or a double covalent bond, or a fluorine atom, covalently bound to another atom, and an electron deficient, or electropositive, hydrogen atom.

The hydrogen atom is typically electron deficient due to the fact that it is covalently bonded to a more electronegative atom such as for example, oxygen or nitrogen. The term "hydrogen bond", as used herein, is interchangeable with the terms "hydrogen bridge" and "cross-linked hydrogen bond".

The terms electronegative and electropositive as used herein will be readily understood by the person skilled in the art to mean the tendency of an atom to attract the pair of electrons in a covalent bond so as to lead to an unsymmetrical distribution of electrons and hence the formation of a dipole moment.

Electronegativity (see pages 14 to 16) and hydrogen bonding (see pages 75 to 79) are discussed more fully in, for example, Advanced Organic Chemistry by J. March, 4$^{th}$ Edition, published by J. Wiley & Sons, 1992.

It is well known in the art that although hydrogen bonds in themselves may be relatively weak, at least compared to covalent and ionic bonds, when a significant number of hydrogen bonds are capable of being formed, for example, between at least two molecules, the overall interaction between the at least two molecules may be relatively strong.

The hydrogen-bonding moieties according to the present invention have at least three groups that are capable of forming a hydrogen bond with the same or different moieties. The moieties may be those in the same polymer molecule or, alternatively, with the same or different moieties in a different polymer molecule according to the present invention ie, the hydrogen bonds formed between the polymers of the present invention may be intramolecular but preferably they are intermolecular.

The hydrogen-bonding moieties, as defined herein, include any optional linker groups connecting the hydrogen-bonding moieties to the polymeric, oligomeric or monomeric linker.

The polymer according to the present invention satisfies two requirements, ie, the combination of the ability to form intermolecular hydrogen bonds and having at least two hydrogen-bonding moieties capable of hydrogen bonding to each other, to form so-called "supramolecular arrays".

Supramolecular arrays are non-covalently bonded assemblies of molecules, typically with two or three-dimensional ordering, which are usually formed reversibly under thermodynamic control. The arrays can be oligomeric or polymeric, depending on, for example, factors such as the concentration of the "monomer" and the shape of the "monomer". The term monomer may in this general context refer to a polymeric or monomeric species but in the context of the present invention will be restricted to the at least one hydrogen bonding polymer.

Thus, the at least one hydrogen bonding polymer according to the present invention may suitably be present in cosmetic or personal care compositions according to the present invention or on hair treated with the polymers or compositions of the invention as at least one, preferably more than one, distinct supramolecular array. Where more than one supramolecular array is present, the arrays may have the same or varying size ie, the number of "monomeric" hydrogen bonding polymers may be the same or different. As will be appreciated by the person skilled in the art, the size of the supramolecular array or arrays will depend on the particular physical conditions such as concentration and temperature.

Alternatively, the hydrogen-bonding polymer according to the present invention may be present in the form of both a supramolecular array or arrays (which includes arrays of two or more polymers) and the "monomeric" polymer form or may exist wholly in the "monomeric" polymer form.

The hydrogen-bonding moieties comprising the polymer of the present invention may also be capable of forming hydrogen bonds both to and between naturally occurring polymers such as, for example, keratin as well as other polymers, such as for example, man-made polymers, for example nylon and terylene. The hydrogen bonds may be formed either to or between hydrogen-bonding moieties present either wholly or partially as part of a supramolecular array or may only form part of the "monomeric" hydrogen-bonding polymer.

It is desirable that the at least one polymer according to the present invention is substantially linear. It is also preferable that the hydrogen-bonding moiety has an essentially flat structure. In a particularly preferred embodiment, the conformation of the hydrogen-bonding moiety is restricted by the formation of an intramolecular hydrogen bond.

Suitably the hydrogen-bonding moiety comprises a structural element, or building block, having the general formula (I), (II) or (III)

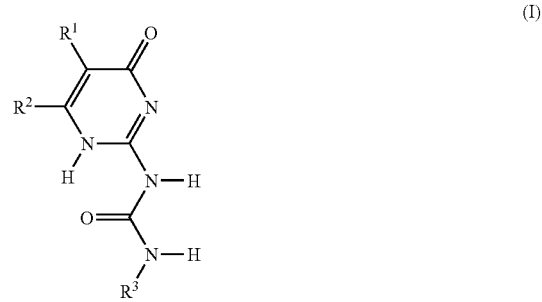

(I)

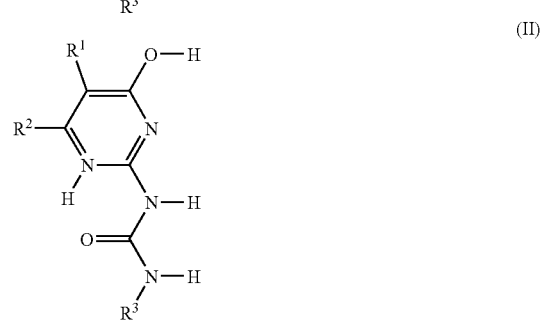

(II)

-continued

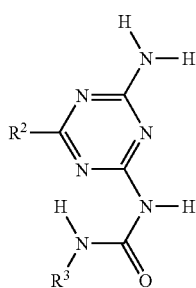

(III)

wherein $R^1$ is H, $C_1$-$C_{24}$ alkyl, $C_{2-24}$ alkenyl, $C_{2-24}$ alkynyl aryl, aralkyl or heteroaryl, optionally substituted, preferably H, and $R^2$ and $R^3$ may be either a covalent linking unit, linking the hydrogen-bonding moiety to a polymeric, oligomeric or monomeric linker, or a side group selected from H, $C_1$-$C_{24}$ alkyl, $C_{2-24}$ alkenyl, $C_{2-24}$ alkynyl, aryl, aralkyl or heteroaryl groups optionally substituted, or polyoxyethylene or polyoxypropylene or a random or block copolymer thereof. Preferably, one of $R^2$ and $R^3$ is H, polysiloxy, $C_1$-$C_{18}$ alkyl, more preferably $C_6$-$C_{18}$ alkyl. $R^2$ and $R^3$ are not both side groups. Most preferably $R^2$ is a methyl group.

Also suitable for use as a preferred hydrogen bonding moiety is trimellitic acid (TMA) (benzene-1,2,4-tricarboxylic acid), and derivatives thereof. The general structure of trimellitic acid is given below:

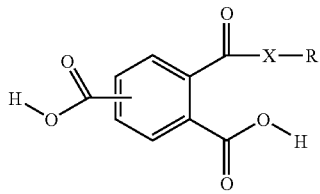

Where X is oxygen or an amide (NH) group and R is either a covalent linking unit, linking the hydrogen-bonding moiety to a polymeric, oligomeric or monomeric linker, or a side group selected from H, $C_1$-$C_{24}$ alkyl, $C_{2-24}$ alkenyl, $C_{2-24}$ alkynyl, aryl, aralkyl or heteroaryl groups optionally substituted, or polyoxyethylene or polyoxypropylene or a random or block copolymer thereof. Preferably, R is H, polysiloxy, $C_1$-$C_{18}$ alkyl, more preferably $C_6$-$C_{18}$ alkyl, most preferably R is a methyl group.

The position of the two carboxylic acid groups can either be in a meta (1,3-) or para (1,4-) arrangement with respect to each other or a random mixture of both.

The term "alkyl" as used herein, includes straight chain and, for alkyl groups containing three or more carbon atoms, branched and also cycloalkyl groups. The cycloalkyl groups may optionally contain a heteroatom selected from nitrogen, oxygen and sulfur. Examples of straight chain alkyl include methyl, ethyl, propyl, butyl, pentyl, hexyl, heptyl, octyl, nonyl, decyl, undecyl, dodecyl, tridecyl and C14, C15, C16, C17 C18, C19 C20, C21 C22, C23 and C24 linear alkyl. Examples of branched alkyl include isopropyl, isobutyl, and tert-butyl. Examples of cycloalkyl groups include cyclopropyl, cyclobutyl, cyclopentyl and cyclohexyl.

The alkyl groups may optionally be substituted with, for example, aryl, aralkyl and heteroaryl groups as defined below and/or one or more groups such as, for example, amino, fluorine, chlorine, bromine, iodine, nitro, phenyl, hydroxy, sulfide, thiol, ester (ie, —$CO_2$—$R^{3a}$ where $R^{3a}$ is selected from: $C_{1-6}$ unsubstituted alkyl, $C_{2-6}$ alkenyl or $C_{2-6}$ alkynyl; and aralkyl, aryl, heteroaryl or heteroaralkyl as defined herein), and amide (ie, —$CONR^{4a}R^{5a}$ where $R^{4a}$ and $R^{5a}$ are independently selected from: hydrogen; $C_{1-6}$ unsubstituted alkyl, $C_{2-6}$ alkenyl or $C_{2-6}$ alkynyl; and aryl, aralkyl, heteroaryl and heteroaralkyl groups as defined herein). Alkyl groups may be substituted in the alkyl chain by one or more keto groups and/or heteroatoms selected from O, S and NH.

The terms "alkenyl" and "alkynyl" are defined similarly to the term "alkyl" but the groups contain one or more carbon-carbon double or triple bonds, respectively.

The term "aryl" as used herein includes phenyl and other polycyclic fused ring compounds which contain at least one fully aromatic ring, such as, for example, naphthalene and 3,4-dihydronaphthalene, optionally substituted with one or more groups such as, for example, amino, fluorine, chlorine, bromine, iodine, nitro, phenyl, hydroxy, sulfide, thiol, ester (ie, —$CO_2$—$R^{3b}$ where $R^{3b}$ is selected from: $C_{1-6}$ unsubstituted alkyl, $C_{2-6}$ alkenyl or $C_{2-6}$ alkynyl; and aralkyl as defined herein), and amide (ie, —$CONR^{4b}R^{5b}$ where $R^{4b}$ and $R^{5b}$ are independently selected from: hydrogen; $C_{1-6}$ unsubstituted alkyl, alkenyl or alkynyl; and aralkyl, groups as defined herein).

The term "aralkyl" as used herein refers to $C_1$ to $C_6$ alkyl substituted with aryl (eg, benzyl).

The term "heteroaryl" as used herein refers to monocyclic and polycyclic fused or non-fused ring containing compounds containing at least one heteroatom such as, for example, nitrogen, sulfur or oxygen or mixtures thereof within any of the rings and where at least one of the rings is aromatic. The ring or rings comprising the heteroatom may be three, four, five, six, seven or eight membered. The term "heteroaryl" is intended to include compounds that comprise partially or fully saturated rings, in addition to aromatic rings. The heteroatom may be situated in the partially or fully saturated rings or in the aromatic ring.

Non-limiting examples of such heteroaryl compounds include aryl-substituted piperazines, azo compounds, pyrazoles, thiazoles, oxazoles, 1,2,4-triazoles, benzothiazoles, benzotriazoles, pyrimidines, thiadiazines, pyridines, thiophenes, azepines carbazoles, triazines, purines, pyrimidinones, pyridones, quinolines and iso-quinolines.

The term "heteroaralkyl" as used herein refers to $C_1$ to $C_6$ alkyl substituted with heteroaryl (eg, pyrazolylmethyl). The heteroaryl compounds may optionally be substituted with alkyl, alkaryl or aryl groups as defined above or with one or more other groups selected from, for example, amino, fluorine, chlorine, bromine, iodine, nitro, phenyl, hydroxy, sulfide, thiol, ester (ie, —$CO_2$—$R^{3c}$ where $R^{3c}$ is selected from: $C_{1-6}$ unsubstituted alkyl, $C_{2-6}$ alkenyl or $C_{2-6}$ alkynyl; and aralkyl as defined herein), and amide (ie, —$CONR^{4c}R^{5c}$ where $R^{4c}$ and $R^{5c}$ are independently selected from: hydrogen; $C_{1-6}$ unsubstituted alkyl, $C_{2-6}$ alkenyl or $C_{2-6}$ alkynyl; and aralkyl, groups as defined herein). Heteroaryl groups may comprise keto groups in the aromatic ring.

Preferably $R^1$ is H, $R^2$ is a $C_1$-$C_{18}$ alkyl group and $R^3$ is a covalent linking unit, linking the hydrogen-bonding moiety to a polymeric, oligomeric or monomeric linker.

The covalent linking unit desirably comprises any functional group and/or spacer group to which the polymeric, oligomeric or monomeric linker may be attached by the formation of a covalent bond, for example one or more amide and/or ester and/or urea linkages. The covalent linking unit preferably also comprises $C_1$-$C_{24}$ alkylene, $C_{2-24}$ alkenylene, $C_{2-24}$ alkynylene, arylene, aralkylene or heteroarylene groups, optionally substituted. The functional group may be modified or removed on formation of the covalent bond. Preferably the functional group is the derivative of an isocyanate (eg, —NH—C(O)—K, wherein K is O or NH) and the spacer group is a $C_{1-16}$ alkylene group.

The at least one polymeric, oligomeric or monomeric linker may be any polymer or oligomer or monomer and is preferably a linker which is understood by the skilled person to be flexible. Preferably, the at least one polymeric, oligomeric or monomeric linker is a polymer or oligomer. In particular, the term "flexible polymer or oligomer" is intended to mean a polymer or oligomer whose backbone is able to adopt a range of different possible non-linear conformations and wherein said different non-linear conformations are readily interconvertable with each other at temperatures at which the compositions of the invention will be used. It will be understood that the flexibility of the backbone will depend on the nature of the groups in the backbone and that rigid, for example aryl, groups in the backbone will reduce the degree of flexibility.

Preferably, the backbone of the polymeric, oligomeric or monomeric linker comprises a sufficient number of single covalent bonds, such as for example, carbon-carbon single bonds, carbon-oxygen single bonds, silicon-oxygen single bonds and carbon-nitrogen single bonds in order to maintain flexibility.

The at least one polymeric, oligomeric or monomeric linker may have any of the polymer structures or architectures known in the art. Thus, the at least one flexible polymer suitably comprises structures such as, for example: a linear, branched or hyperbranched homopolymer; an alternating copolymer; a graft copolymer; a random copolymer; a block copolymer; or a dendritic or starburst structure; or combinations of the above structures. Suitable polymeric, oligomeric or monomeric linkers are those, for example, selected from the group consisting of: polysiloxanes; polysilicones; polyethers; polyesters; polyamides; polyurethanes; polyureas; polyacrylates; polymethacrylates; polyacrylamides; polyvinylacetate; polyvinylalcohol; polyethylene; polybutylene; polybutadiene; vinyl derived polymers or combinations thereof (including random and block copolymers). These polymers may be obtained commercially from, for example, Sigma-Aldrich Chemical Co., BASF or ISP, or synthesised according to any of the methods known to the person skilled in the art.

Preferably the polymeric, oligomeric or monomeric linker is selected from polysiloxanes, polyethers, polyethylenes and/or mixtures thereof.

The hydrogen-bonding moiety may, for example, form an integral part of the backbone of the polymeric, oligomeric or monomeric linker, and so have more than one, possibly, for example, from two to ten polymeric, oligomeric or monomeric linkers covalently bound to suitable groups comprising the hydrogen-bonding moiety which polymeric linkers so bound are covalently bound to at least one further hydrogen-bonding moiety.

The at least two hydrogen-bonding moieties may form both an integral part of the polymeric, oligomeric or monomeric linkage and/or occupy the terminal positions at the end of the polymeric, oligomeric or monomeric linker and/or be present at positions along the backbone of the polymer.

Preferably, however, the at least two hydrogen-bonding moieties, which are the same or different, occupy the terminal position on the at least one polymeric, oligomeric or monomeric linker and the polymeric, oligomeric or monomeric chain is covalently bound to each hydrogen-bonding moiety via one position.

In one embodiment, the hydrogen bonding polymer according to the present invention comprises a polymer of formula $A(YX)_n$ wherein n is at least 2 and X is a hydrogen-bonding moiety and each X is the same or different and has at least 3 groups capable of forming a hydrogen bond to another same or different X group and each Y is the same or different and is a polymeric, oligomeric or monomeric linking group and A is a core of valency n and can be a monomer part of Y when n is 2.

The core A suitably comprises any molecule or polymer to which the polymeric, oligomeric or monomeric linker and the hydrogen-bonding moiety can be covalently bound. Thus, A may be selected from a single functionalised molecule, such as for example an aryl group or a sugar molecule or may comprise any polymeric species, in which case the $(YX)_n$ unit may be grafted onto the backbone of the polymer or be incorporated during the synthesis of the polymer. The value of n will thus be limited by the nature of A. Preferably n has a value of from 2 to 1000, more preferably from 2 to 100, particularly preferably from 2 to 20.

In a preferred embodiment of the present invention, the hydrogen bonding polymer comprises a polymer of formula $Y(-X)_n$ wherein each hydrogen-bonding moiety X is the same or different and has at least 3 groups capable of forming a hydrogen bond to the same or different X group and n is an integer of from 2 to 6, preferably 2, and Y is a polymeric, oligomeric or monomeric linker group.

Preferably, X is a hydrogen-bonding moiety comprising a heterocycle selected from a triazine and/or a pyrimidone, more preferably, the heterocycle is selected from the compounds having formula (I), (II) or (III) and mixtures thereof. Preferably, Y is a substantially linear polymer selected from polysiloxanes, polyethers and polyethylenes.

Preferably, the hydrogen-bonding polymer according to the present invention has the structure indicated by formula IV:

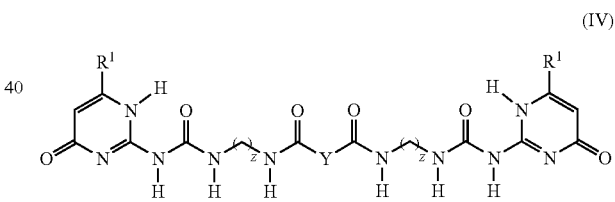

(IV)

wherein z is an integer from 1-16, preferably 2 to 12, more preferably 4 to 10 eg, 6;

and $R^1$ is selected from H, $C_1$-$C_{24}$ alkyl, $C_{2-24}$ alkenyl, $C_{2-24}$ alkynyl, aryl, aralkyl or heteroaryl groups all optionally substituted, preferably $C_1$-$C_{18}$ alkyl, more preferably $C_6$-$C_{18}$ alkyl, most preferably a methyl group.

and wherein Y is selected from poly(ethylene/butylene) random or block copolymers

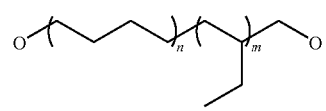

wherein n and m are integers such that the molecular weight of the hydrogen-bonding polymer is in the range of from 500 to 50,000 g/mol and in a particularly preferred embodiment is approximately 3,500 g/mol;

poly(tetramethylene oxide)

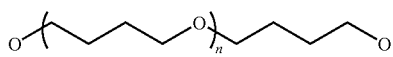

in which n is an integer such that the molecular weight of the hydrogen-bonding polymer is in the range of from 500 to 50,000 g/mol and in a particularly preferred embodiment is approximately 2000 g/mol;

poly(ethylene oxide)

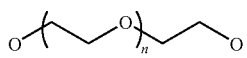

in which n is an integer such that the molecular weight of the hydrogen bonding polymer is in the range of from 500 to 50,000 g/mol, and in a particularly preferred embodiment is approximately 2000 g/mol; and polysiloxane

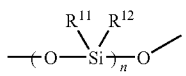

wherein $R^{11}$ and $R^{12}$ are independently selected from $C_1$-$C_{24}$ alkyl, $C_{2-24}$ alkenyl, $C_{2-24}$ alkynyl, aryl, aralkyl or heteroaryl, each of which may be optionally substituted, for example with hydroxyl or amino groups, or where $R^{11}$ and $R^{12}$ are alkyl, optionally substituted at the end of or in the alkyl chain with one or more —O— linkages, or at least one of $R^{11}$ and $R^{12}$ is polyoxyethylene or polyoxypropylene or a random or block copolymer thereof, and n is an integer from 20 to 100,000. Preferably $R^{11}$ and $R^{12}$ are independently $C_1$-$C_{12}$ alkyl, more preferably both $R^{11}$ and $R^{12}$ are methyl. More preferably, n is an integer such that the molecular weight of the hydrogen-bonding polymer is in the range of from 800 to 50,000 g/mol and in a particularly preferred embodiment is approximately 1000 to 6000 g/mol.

Also preferred is the hydrogen-bonding polymer having the structure below:

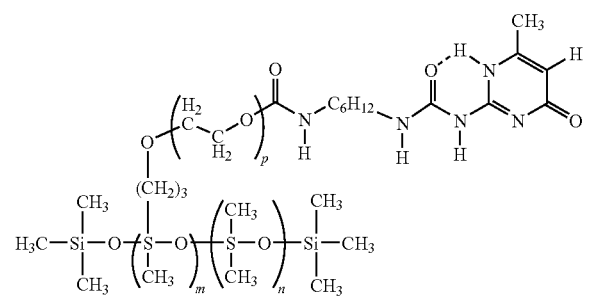

where m, n and p are such that the molecular weight of the polymer is from 500 to 50,000 g/mol, a particularly preferred embodiment having a molecular weight of approximately 6,000 g/mol The molecular weights cited in this specification refer to the number average molecular weight $M_n$.

From the above description it can be seen that in general the hydrogen bonding polymers of the invention have a molecular weight range form 500 to 50,000 g/mol, more preferably from 1,000 to 20,000 g/mol, most preferably from 1,000 to 10,000 g/mol. These molecular weight ranges are particularly advantageous as they do not have sensory negatives such as making the hair feel sticky.

When the polymer of the invention has low solubility in water (ie, such that it is insufficiently soluble to provide a benefit in compositions of the invention), it is preferably used together with a solvent for the polymer. For example, when Y in the above formula is polysiloxane, the polymer is preferably used together with a volatile silicone in the composition. The silicone may be in the form of an emulsion. Cosmetically acceptable volatile silicones are well known in the art.

It is preferable if the hydroge bonding polymer is not a siloxane/urea copolymer.

The polymer according to the present invention may suitably be produced by reacting a preformed flexible polymer precursor functionalised with nucleophilic or electrophilic groups with a hydrogen-bonding moiety with corresponding electrophilic or nucleophilic groups respectively. Suitable nucleophilic groups include those such as, for example, primary or secondary alkyl or aryl amino groups, thiols, hydroxyl, alkoxide groups or mixtures thereof. Suitable electrophilic groups include those such as, for example, keto or aldehyde carbonyl, esters, acyl halides, such as acid chlorides or bromides, acid anhydrides, carboxylic acids converted into so called "activated esters", nitriles, isocyanates and alkyl halides, wherein the halide is preferably selected from chloride, bromide or iodide.

Suitably, the covalent bond forming reaction is selected from any of those commonly used in the art for the construction of molecular architectures, such as, for example, nucleophilic substitution, nucleophilic addition, electrophilic substitution or electrophilic addition.

In the case of nucleophilic substitution and nucleophilic addition reactions suitable for combining the hydrogen-bonding moiety and the polymeric, oligomeric or monomeric linker precursor by the formation of a covalent bond, either the hydrogen-bonding moiety or the preformed polymeric, oligomeric or monomeric linker may comprise at least one suitable nucleophilic group and at least one suitable electrophilic group.

Alternatively, the hydrogen-bonding moiety and the polymeric, oligomeric or monomeric linker precursor may suitably be combined by the formation of a covalent bond by, for example, radical reactions, or between a diene and a dienophile in a Diels-Alder type reaction, or hydrosilation.

The polymeric, oligomeric or monomeric linker may suitably be formed in situ by derivatising a hydrogen-bonding moiety with, for example, a vinyl group. Thus, the vinyl derivatised hydrogen-bonding moiety comprises a monomer that may be copolymerised with any suitable vinyl monomer known in the art to form part or all of the flexible polymer linker.

Other suitable monomers for in situ polymer formation include the epoxy-chlorohydrin monomer, for example.

The polymeric, oligomeric or monomeric linker precursor may suitably comprise at least two nucleophilic or electrophilic groups. Preferably, the preformed flexible polymer linker comprises two nucleophilic groups. More preferably, the preformed flexible polymer linker comprises two nucleophilic groups, such as, for example, those selected from —OH, —O⁻, —NH$_2$, —NR$^{1d}$H, —SH or —S⁻, wherein R$^{1d}$ is selected from $C_{1-12}$ alkyl, $C_{2-12}$ alkenyl or $C_{2-12}$ alkynyl.

Preferably the polymeric, oligomeric or monomeric linker precursor according to the invention is a polymeric, oligomeric or monomeric diol. By polymeric diol, it is intended to mean a polymeric chain comprising at least two terminal hydroxyl groups. The polymeric, oligomeric or monomeric diol may be obtained commercially or may be synthesised according to any of the methods known in the art.

The polymeric diol may comprise other functional groups or atoms within the backbone of the polymer such as, for example, oxygen atoms.

The amount of hydrogen bonding polymer used in the compositions according to the invention is suitably from 0.1 to 20% by weight of the total composition, preferably from 0.25 to 10% by weight of the total composition, more preferably from 0.5 to 5% by weight of the total composition.

The compositions of the present invention comprise a hair conditioning agent and/or a cosmetically acceptable surfactant in an amount of from 0.1 to 50%, preferably, from 1 to 30%, more preferably from 2 to 20% by weight of the total composition.

Suitable hair conditioning agents are, for example, hydrocarbons, silicone fluids, and cationic materials. The hydrocarbons can be either straight or branched chain and can contain from about 10 to about 16, preferably from about 12 to about 16 carbon atoms. Examples of suitable hydrocarbons are decane, dodecane, tetradecane, tridecane, and mixtures thereof. Examples of suitable silicone conditioning agents useful herein can include either cyclic or linear polydimethylsiloxanes, phenyl and alkyl phenyl silicones, and silicone copolyols. Cationic conditioning agents useful herein can include quaternary ammonium salts or the salts of fatty amines.

Examples of cationic conditioning agents include: quaternary ammonium hydroxides, e.g., tetramethylammonium hydroxide, alkyltrimethylammonium hydroxides wherein the alkyl group has from about 8 to 22 carbon atoms, for example octyltrimethylammonium hydroxide, dodecyltrimethy-ammonium hydroxide, hexadecyltrimethylammonium hydroxide, cetyltrimethylammonium hydroxide, octyldimethylbenzylammonium hydroxide, decyldimethyl-benzylammonium hydroxide, stearyldi-methylbenzylammonium hydroxide, didodecyldimethylammonium hydroxide, dioctadecyldimethylammonium hydroxide, tallow trimethylammonium hydroxide, cocotrimethylammonium hydroxide, and the corresponding salts thereof, e.g., chlorides, Cetylpyridinium hydroxide or salts thereof, e.g., chloride, Quaternium-5, Quaternium-31, Quaternium-18, and mixtures thereof.

In hair conditioning compositions according to the invention, the level of cationic surfactant is preferably from 0.01 to 10%, more preferably 0.05 to 5%, most preferably 0.1 to 2% by weight of the composition.

Hair conditioning compositions of the invention may also contain one or more conditioning agents, preferably selected from silicones, protein hydrolysates and quaternised protein hydrolysates and other materials which are known in the art as having desirable hair conditioning properties.

Silicones are the most preferred conditioning agents.

Suitable silicones include volatile and non-volatile silicones, such as for example polyalkylsiloxanes, polyalkylaryl siloxanes, siloxane gums and resins, cyclomethicones, aminofunctional silicones, quaternary silicones and mixtures thereof. Silicone oil is a particularly preferred conditioning agent for hair. The silicone may be in the form of a low viscosity oil which may contain a high viscosity oil or gum in solution. Alternatively, the high viscosity material may be in the form of an emulsion in water. The emulsion may be of high viscosity oil or of a solution of gum in a lower viscosity oil. The particle size of the oil phase may be anywhere in the range from 30 nanometres to up to 20 microns average size.

The silicone oil may suitably be a polydimethylsiloxane with an average particle size of less than 20 microns and preferably less than 2 microns. Small particle size enables a more uniform distribution of silicone conditioning agent for the same concentration of silicone in the composition. Advantageously, a silicone with a viscosity in the range 1-20 million cst is used. The silicone can be cross-linked.

Preferred silicones include polydimethylsiloxanes (of CTFA designation dimethicone) and hydroxylated polydimethylsiloxanes (of CTFA designation dimethiconol). Silicones of the above types are widely available commercially, for example as DC-1784 and DCX2-1391, both ex Dow Corning.

Suitable protein hydrolysates include lauryl dimonium hydroxy propylamino hydrolysed animal protein, available commercially under the trade name LAMEQUAT L, and hydrolysed keratin containing sulphur-bearing amino acids, available commercially under the trade name CROQUAT WKP.

Other suitable hair conditioning agents include fatty alcohols and esters of fatty acids and/or esters of fatty alcohols. Examples of such hair conditioning agents are $C_8$-$C_{24}$ linear alkyl alcohols, $C_1$-$C_{24}$ linear or branched alkyl esters of $C_8$-$C_{24}$ linear alkyl carboxylic acids and $C_8$-$C_{24}$ linear alkyl esters of $C_1$-$C_7$ carboxylic acids.

In accordance with the invention, the composition may also comprise a polymeric water-soluble cationic polymer as a conditioning agent.

The cationic polymer may be present at levels of from 0.01 to 5%, preferably from about 0.05 to 1%, more preferably from about 0.08% to about 0.5% by weight.

Synthetic or naturally derived polymers having a quaternised nitrogen atom are useful. The molecular weight of the polymer will generally be between 5,000 and 10,000,000 Da, typically at least 10,000 Da and preferably in the range 100,000 to about 2,000,000 Da.

Representative synthetic quaternised polymers include, for example: cationic copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA" as Polyquaternium-16); copolymers of 1-vinyl-2-pyrrolidine and dimethylaminoethyl methacrylate (referred to in the industry by CTFA as Polyquaternium-11); cationic diallyl quaternary ammonium-containing polymers including, for example, dimethyldiallylammonium chloride homopolymer (referred to in the industry (CTFA) as Polyquaternium 6); mineral acid salts of amino-alkyl esters of homo- and co-polymers of unsaturated carboxylic acids having from 3 to 5 carbon atoms, as described in U.S. Pat. No. 4,009,256; and cationic polyacrylamides as described in WO95/22311.

Representative naturally-derived quaternised polymers include quaternised cellulosic compounds and cationic guar gum derivatives, such as guar hydroxypropyltrimonium chloride. Examples are JAGUAR C-13S, JAGUAR C-15, and JAGUAR-C17, commercially available from Meyhall in their JAGUAR (trademark) series.

Suitable cationic polyacrylamides are described in WO 95/22311 whose contents are incorporated herein by reference.

Compositions of the invention may comprise at least one cosmetically acceptable surfactant. The surfactant is preferably selected from anionic, nonionic, amphoteric and zwitterionic surfactants, and mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts.

The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$-$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Further nonionic surfactants which can be included in shampoos for the invention are the alkyl polyglycosides (APGs). Typically, the APG is one which comprises an alkyl group connected (optionally via a bridging group) to a block of one or more glycosyl groups. Preferred APGs are defined by the following formula:

$$RO\text{-}(G)_n$$

wherein R is a branched or straight chain alkyl group which may be saturated or unsaturated and G is a saccharide group. Suitable alkyl polyglycosides for use in the invention are commercially available and include for example those materials identified as: Oramix NS10 ex Seppic; Plantaren 1200 and Plantaren 2000 ex Henkel.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The surfactants are present in shampoo compositions of the invention in an amount of from 1 to 50% by weight of the composition, preferably from 1 to 30% by weight.

Compositions of the present invention are preferably formulated into hair care compositions, especially hairspray compositions, but can also be formulated into a wide variety of product types, including mousses, gels, lotions, tonics, sprays, shampoos, conditioners and rinses. It is preferable if the compositions are liquid. Compositions of the invention typically comprise a cosmetically acceptable diluent or carrier. Preferably, the compositions are for use in styling human hair and, more preferably, they are packaged and labelled as such.

Compositions of the invention are not formulated so as to be suitable for use in the laundering of clothes ie, they are not laundry compositions.

Compositions of the invention may, optionally, comprise a fragrance or perfume, preferably in an amount of up to 1% by weight, and/or one or more of the optional additional components described hereinafter.

The carriers and additional components required to formulate such products vary with product type and can be routinely chosen by one skilled in the art. The following is a description of some of these carriers and additional components.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Carriers suitable for use with hair care compositions of the present invention include, for example, those used in the formulation of hair sprays, mousses, tonics, gels, shampoos, conditioners, and rinses. The choice of appropriate carrier will also depend on the particular thermoplastic elastomer to be used, and whether the product formulated is meant to be left on the surface to which it is applied (e.g., hair spray, mousse, tonic, or gel) or rinsed off after use (e.g., shampoo, conditioner, rinse).

The carriers used herein can include a wide range of components conventionally used in hair care compositions. The carriers can contain a solvent to dissolve or disperse the particular thermoplastic elastomer being used, with water, the $C_1$-$C_6$ alcohols, lower alkyl acetate and mixtures thereof being preferred. The carriers can also contain a wide variety of additional materials such as acetone, hydrocarbons (such as isobutane, hexane, decene), halogenated hydrocarbons (such as Freons) and volatile silicones such as cyclomethicone.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Suitable spray containers are well known in the art and include conventional, non-aerosol pump sprays i.e., "atomisers", aerosol containers or cans having propellant, as described above, and also pump aerosol containers utilising compressed air as the propellant.

Where the hair care compositions are conditioners and rinses, the carrier can include a wide variety of conditioning materials. Where the hair care compositions are shampoos, the carrier can include, for example, surfactants, suspending agents, and thickeners. Hair styling creams or gels also typically contain a structurant or thickener, typically in an amount of from 0.01% to 10% by weight.

The carrier can be in a wide variety of forms. For example, emulsion carriers, including oil-in-water, water-in-oil, water-in-oil-in-water, and oil-in-water-in-silicone emulsions, are useful herein. These emulsions can cover a broad range of viscosities, e.g., from about 100 cps to about 200,000 cps. These emulsions can also be delivered in the form of sprays using either mechanical pump containers or pressurised aerosol containers using conventional propellants. These carriers can also be delivered in the form of a mousse. Other suitable topical carriers include anhydrous liquid solvents such as oils, alcohols, and silicones (e.g., mineral oil, ethanol, isopropanol, dimethicone, cyclomethicone, and the like); aqueous-based single phase liquid solvents (e.g., hydro-alcoholic solvent systems); and thickened versions of these anhydrous and aqueous-based single phase solvents (e.g., where the viscosity of the solvent has been increased to form a solid or semi-solid by the addition of appropriate gums, resins, waxes, polymers, salts, and the like).

A wide variety of additional components can be employed in cosmetic and personal care compositions according to the present invention. Examples include the following:

hair styling polymers, other than the polymer of the invention, for hair styling compositions such as hair sprays, gels, and mousses. Hair styling polymers are well known articles of commerce and many such polymers are available commercially which contain moieties which render the polymers cationic, anionic, amphoteric or nonionic in nature. The polymers may be synthetic or naturally derived.

The amount of the hair styling polymer may range from 0.5 to 10%, preferably 0.75 to 6% by weight based on total weight of the composition.

Examples of anionic hair styling polymers are:

copolymers of vinyl acetate and crotonic acid;

terpolymers of vinyl acetate, crotonic acid and a vinyl ester of an alpha-branched saturated aliphatic monocarboxylic acid such as vinyl neodecanoate;

copolymers of methyl vinyl ether and maleic anhydride (molar ratio about 1:1) wherein such copolymers are 50% esterified with a saturated alcohol containing from 1 to 4 carbon atoms such as ethanol or butanol;

acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide); and other compatible unsaturated monomers.

The polymer may also contain grafted silicone, such as polydimethylsiloxane.

Specific examples of suitable anionic hair styling polymers are:

RESYN® 28-2930 available from National Starch (vinyl acetate/crotonic acid/vinyl neodecanoate copolymer);

ULTRAHOLD® 8 available from BASF (CTFA designation Acrylates/acrylamide copolymer);

the GANTREZ®ES series available from ISP corporation (esterified copolymers of methyl vinyl ether and maleic anhydride).

Other suitable anionic hair styling polymers include carboxylated polyurethanes. Carboxylated polyurethane resins are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP-A-0619111 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Amphoteric hair styling polymers which can contain cationic groups derived from monomers such as t-butyl aminoethyl methacrylate as well as carboxyl groups derived from monomers such as acrylic acid or methacrylic acid can also be used in the present invention. One specific example of an amphoteric hair styling polymer is Amphomer® (Octylacrylamide/acrylates/butylaminoethyl methacrylate copolymer) sold by the National Starch and Chemical Corporation.

Examples of nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Other suitable nonionic hair styling polymers are cross-linked silicone resins or gums. Specific examples include rigid silicone polymers such as those described in EP-A-0240350 and cross-linked silicone gums such as those described in WO 96/31188.

Examples of cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic hair styling polymers are:

copolymers of N-vinylpyrrolidone and dimethylaminoethyl methacrylate, available from ISP Corporation as Copolymer 845, Copolymer 937 and Copolymer 958;

copolymers of N-vinylpyrrolidone and dimethylaminopropylacrylamide or methacrylamide, available from ISP Corporation as Styleze® CC10;

copolymers of N-vinylpyrrolidine and dimethylaminoethyl methacrylate;

copolymers of vinylcaprolactam, N-vinylpyrrolidone and dimethylaminoethylmethacrylate;

Polyquaternium-4 (a copolymer of diallyldimonium chloride and hydroxyethylcellulose);

Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;

Polyquaternium-16 (formed from methylvinylimidazolium chloride and vinylpyrrolidone), available from BASF as Luviquat® FC 370, FC 550, FC 905 and HM-552;

Polyquaternium-46 (prepared by the reaction of vinylcaprolactam and vinylpyrrolidone with methylvinylimidazolium methosulphate), available from BASF as Luviquat®Hold.

Examples of suitable naturally-derived hair styling polymers include shellac, alginates, gelatins, pectins, cellulose derivatives and chitosan or salts and derivatives thereof. Commercially available examples include Kytamer® (ex Amerchol) and Amaze® (ex National Starch).

Also suitable for use as optional components in the compositions of the invention are the ionic copolymers described in WO 93/03703, the polysiloxane-grafted polymers disclosed in WO 93/23446, the silicone-containing polycarboxylic acid copolymers described in WO 95/00106 or WO 95/32703, the thermoplastic elastomeric copolymers described in WO 95/01383, WO 95/06078, WO 95/06079 and WO 95/01384, the silicone grafted adhesive polymers disclosed in WO 95/04518 or WO 95/05800, the silicone macrografted copolymers taught in WO 96/21417, the silicone macromers of WO 96/32918, the adhesive polymers of WO 98/48770 or WO 98/48771 or WO 98/48772 or WO 98/48776, the graft polymers of WO 98/51261 and the grafted copolymers described in WO 98/51755.

With certain of the above-described polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanolamine (DIPA); triisopropanolamine (TIPA); and dimethyl stearamine (DMS). A long chain amine neutralising agent such as stearamidopropyl dimethylamine or lauramidopropyl dimethylamine may be employed, as is described in U.S. Pat. No. 4,874,604. Also suitable are inorganic neutralisers, examples of which include sodium hydroxide, potassium hydroxide and borax. Mixtures of any of the above neutralising agents may be used. Amounts of the neutralising agents will range from about 0.001 to about 10% by weight of the total composition.

- sunscreening agents such as 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof.
- anti-dandruff actives such as zinc pyrithione, piroctone olamine, selenium disulphide, sulphur, coal tar, and the like.
- carboxylic acid polymer thickeners for hair shampoo and conditioner compositions. These crosslinked polymers contain one or more monomers derived from acrylic acid, substituted acrylic acids, and salts and esters of these acrylic acids and the substituted acrylic acids, wherein the crosslinking agent contains two or more carbon-carbon double bonds and derived from a polyhydric alcohol. Examples of carboxylic acid polymer thickeners useful herein are those selected from the group consisting of carbomers, acrylates/$C_{10}$-$C_{30}$ alkyl acrylate crosspolymers, and mixtures thereof. Compositions of the present invention can comprise from about 0.025% to about 1%, more preferably from about 0.05% to about 0.75% and most preferably from about 0.10% to about 0.50% of the carboxylic acid polymer thickeners, by weight based on total weight of the composition.
- emulsifiers for emulsifying the various carrier components of the compositions of the invention. Suitable emulsifier types include polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, and mixtures thereof. The emulsifiers can be used individually or as a mixture of two or more and can comprise from about 0.1% to about 10%, more preferably from about 1% to about 7%, and most preferably from about 1% to about 5%, by weight based on total weight of the composition.
- vitamins and derivatives thereof (e.g., ascorbic acid, vitamin E, tocopheryl acetate, retinoic acid, retinol, retinoids, and the like).
- preservatives, antioxidants, chelators and sequestrants; and aesthetic components such as fragrances, colourings, hair nutrients and essential oils.

The method of the invention comprises applying a hydrogen-bonding polymer as described herein to the hair. The polymer is preferably in the form of a composition of the invention when it is applied to the hair, although other product forms may also be used, such as for example a simple solution of the polymer.

The method of the invention may involve the conventional steps in hair treatment methods. For example, the method may involve shampooing and/or conditioning (either as part of shampooing or in a separate process step) and/or styling the hair. The polymer is suitably applied to the hair at any one or more or all of these steps.

The method of the invention may comprise the step of heating the hair during or after (preferably after) the polymer is applied to the hair. For example, the hair may be heated to a temperature of about 40° C. to about 90° C., more preferably about 50° C. to about 80° C. Hair may be heated, for example, as part of a hair drying process, such as using a hair drier eg, during blow drying. Without wishing to be bound by theory, it is believed that heating the hair may improve the beneficial properties of the polymer on the hair, for example by giving improved film formation.

The following non-limiting Examples further illustrate the preferred embodiments of the invention. All percentages referred to in the examples and throughout this specification are by weight based on total weight unless otherwise indicated.

EXAMPLES

Synthesis of Materials

The polymers of the invention are prepared according to the method described by Folmer B J B, Sijbesma R P, Versteegan R M, van der Rijt J A J, Meijer E W, Advanced Materials, 12, 874, 2000. Polymers A, B and C are prepared by using the appropriate OH functional polymer.

Polymer A, B and E have the generic structure (VII) given for a bis-functional material, where Y is a spacer polymer.

Polymers D and E are graft functional materials and have their complete structure drawn, these do not conform to the generic structure (VII).

Polymer A

Formula VII in which Y is poly(ethylene oxide)

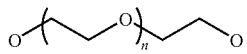

in which n is an integer such that the molecular weight of the hydrogen bonding polymer is approximately 2000 g/mol.

Polymer B

Formula VII in which Y is Pluronic F108

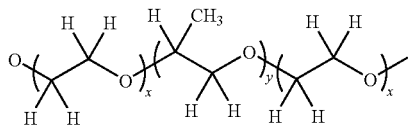

In which n and m are integers such that the molecular weight of the hydrogen-bonding polymer is approximately 16700 g/mol;

Polymer C (Graft polymer)

Formula VIII, The complete repeating structure is 98% hydrolysed polyvinyl alcohol containing 1% functionality N with respect to L+M+N (VIII)

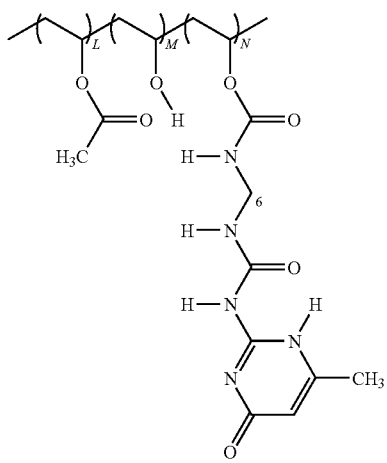

in which L, M and N are integers such that the molecular weight of the hydrogen-bonding polymer is approximately 22000 g/mol.

Polymer D (Graft Polymer)

Formula VIII, The complete repeating structure is 98% hydrolysed polyvinyl alcohol containing 5% functionality N with respect to L+M+N in which L and M and N are integers such that the molecular weight of the hydrogen-bonding polymer is approximately 22000 g/mol.

(VIII)

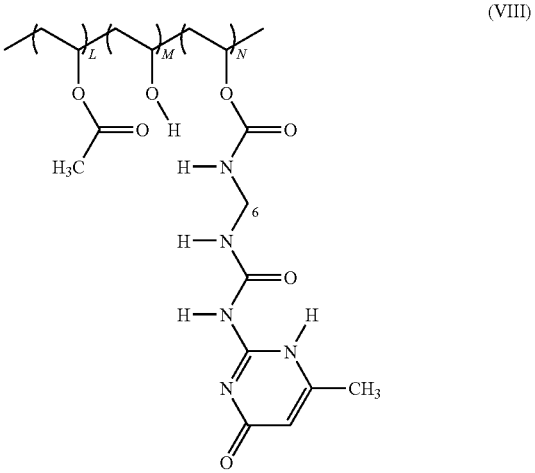

Polymer E

Formula VII in which Y is hydroxyethoxypropyl terminated Polydimethyl siloxane

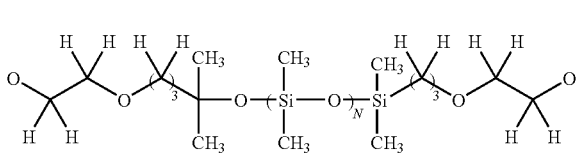

Polymer F (TMA functionalised Poly(ethylene glycol)).

(IX)

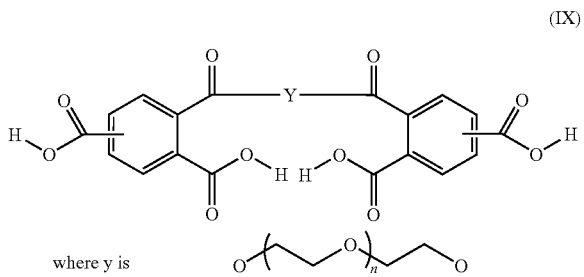

in which n is an integer such that the molecular weight of the polymer is approximately 8,000.

Poly(ethylene glycol) of average molecular weight 8000 (16.00 g, 2 mmol) was dissolved in toluene (130 mL) in a round bottom flask. The apparatus was fitted with a Dean and Stark trap and the solution brought to reflux for 12 hours. Trimellitic anhydride (1.153 g, 6 mmol) was added, as a solid to the anhydrous solution, then heating was resumed and the mixture kept at reflux for 6 hours. The reaction mixture was allowed to cool to 50 deg. C. before silica gel 60H (2.0 g) was added. The suspension was stirred for 20 min. then filtered to remove the insoluble silica. The filtrate was evaporated to leave a white solid which was dried in a vacuum oven overnight to give the TMA-functionalised polymer (15.5 g). The material was readily soluble in chloroform, toluene and water.

FTIR (solid) 2985, 1725, 1405 cm$^{-1}$.

$^1$H NMR (500 MHz; CDCl$_3$) 3.50-3.85 (1000H, m, Peg backbone CH$_2$—CH$_2$—O); 4.47 (4H, m, 2×CH$_2$ at termini of PEG chain); 7.78 (2H, m, 2×CH), 8.20 (2H, m, 2×CH), 8.43 (2H, m, 2×CH) aromatic CH's in trimellitic skeleton.

Example 1

Application to Hair

DMA Protocol

A TA Instruments Dynamic Mechanical Analyser (DMA) 2980 was used to measure physical properties of hair arrays with the instrument operating in a 3 point bending mode. The wet hair array was placed on the 5 mm bending clamp and the DMA chamber was programmed to heat from ambient to 100° C. at 3° C./minute and cool to 10° C. at the same rate. An off-set force or static force of 0.07 N was applied to the hair array and the applied dynamic force was varied during the temperature cycle to maintain a fixed oscillation amplitude of 20 μm at an oscillation frequency of 1 Hz. The auto-tension level was set to 150% to guarantee that the static force would increase in line with the dynamic force and therefore keep the measurements stable over a wide range of applied forces. A number of physical properties of the array were measured throughout the heating and cooling cycle. The storage modulus was found to correlate well to the perceived stiffness of the hair array and gives a clear indication of style creation and hold properties.

Preparation of Hair Arrays 2 g of 254 mm (10") Spanish hair was used to make hair bundles for DMA measurements. 250 fibres with diameters between 60-70 μm were gathered into a bundle of 5 mm diameter, 1 mm depth and adhesive was applied at 2 cm intervals along the array. When the adhesive was set, the hair switch was cut using a scalpel at the adhesive joints to give eight 2 cm bundles per switch. The tip-ends of the fibres were not used for DMA measurements.

Treatment

The hair arrays were weighed before application of 2 drops of polymer solution (typically 1-4 weight %) and the treatment was massaged into the array. The weight of the wet switch was then recorded and the ratio of weights of treatment to dry array noted (typically 0.3-0.4). The storage modulus data was normalised to give a weight ratio of 0.35 for all samples.

Results

| | Storage modulus values | |
|---|---|---|
| Treatment (weight % in solution) | Storage Modulus (during heating) (MPa) | Storage Modulus (after heating) (Mpa) |
| Clean hair | 53.4 | 66.9 |
| Conventional conditioner | 37.3 | 48.9 |
| Polymer A 3% | 93.7 | 1212.4 |
| Polymer A 3% plus Gafquat 755N 1% | 570.0 | 1295.6 |
| Gafquat 755N 1% | 951.7 | 793.8 |

-continued

| | Storage modulus values | |
|---|---|---|
| Treatment (weight % in solution) | Storage Modulus (during heating) (MPa) | Storage Modulus (after heating) (Mpa) |
| Polymer B 1% | 86.7 | 389.9 |
| Polymer C 1% | 85.4 | 134.9 |

Gafquat 755N is Polyquaternium-11 from ISP

For Polymers A, B and C and Polymer A/Gafquat 755N blend, the chamber was raised and cooling took place under ambient conditions (21° C., 40% RH) to confirm that the high levels of storage modulus were maintained in the presence of humidity. For the remaining experiments, the chamber maintained an atmosphere of dried air throughout the experiment.

The results show that the polymers of the invention provide stiffening and therefore styling benefits when applied to hair. The results also show that this effect is enhanced after the hair is heat treated.

Examples 2 to 9

Compositions of the Invention

The following are examples of compositions of the invention.

The materials in the examples include the following:

| Material | Supplier | Function |
|---|---|---|
| Silicone emulsion X2 1787 ™ | Dow Corning | conditioning |
| VOLPO CS 50 ™ | Croda Chemicals | surfactant |
| Sepicide LD ™ | Seppic | preservative |
| Cremophor RH410 ™ | BASF | stabiliser |
| Silicone DC 200/DC 24 S ™ | Dow Corning | conditioning |
| Silwet L7602/L-720 ™ | Union Carbide | surfactant |
| CAP 40 ™ | Calor Gas | propellant |
| Carbopol 980 ™ | BF Goodrich | structurant |
| Jaguar HP-105 ™ | Rhodia | conditioning |
| Silicone Fluid 245 ™ | Dow Corning | conditioning |

Ethanol is SD Alcohol 40-B (92% active)

Example 2

A styling mousse is formulated as follows:

| Material | % in product (w/w) |
|---|---|
| Silicone Emulsion X2 1787 | 1.2 |
| Polymer A, B, C or D | 1.5 |
| VOLPO CS 50 | 0.3 |
| Sepicide LD | 0.4 |
| Cremophor RH410 | 0.2 |
| Ethanol | 7.5 |
| CAP 40 | 8.0 |
| Perfume | 0.2 |
| Water | to 100% |

Example 3

A hairspray is formulated as follows:

| Material | % in product (w/w) |
| --- | --- |
| Polymer A, B, C or D | 3.0 |
| Silicone DC200 | 0.09 |
| Silwet L7602 | 0.09 |
| CAP 40 | 35.0 |
| Ethanol | 60.0 |
| Perfume | 0.10 |
| Water | to 100% |

Example 4

A pump spray is formulated as follows:

| Material | % w/w |
| --- | --- |
| Ethanol | 60.0 |
| Polymer A, B, C or D | 3.5 |
| Silwet L-720 | 0.3 |
| Silicone DC24S | 0.15 |
| Fragrance | 0.3 |
| Water | to 100% |

Example 5

A styling gel is formulated as follows:

| Material | (a) % w/w | (b) % w/w |
| --- | --- | --- |
| Polymer A, B, C or D | 3.8 | — |
| Polymer E | — | 1.0 |
| Carbopol 980 | 0.4 | 0.4 |
| Water | to 100% | To 100% |
| Sepicide LD | 0.4 | 0.4 |
| Sodium hydroxide (8% 2M) | 0.1 | 0.1 |
| Ethanol | 10.0 | — |
| Cremaphor RH410 | 0.4 | 0.4 |
| Jaguar HP-105 | 0.2 | 0.2 |
| Perfume | 0.15 | 0.15 |
| Silicone DC 245 | — | To 10% |

Example 6

A 55% voc propelled aerosol composition is formulated as follows:

| Material | % w/w |
| --- | --- |
| Polymer A, B, C or D | 3.75 |
| Silicone Fluid 245 | 0.20 |
| Fragrance | 0.32 |
| Ethanol | 19.53 |
| Dimethyl ether | 35.00 |
| Sodium benzoate | 0.26 |
| Cyclohexylamine | 0.21 |
| Water | to 100% |

Example 7

A 55% voc pump hairspray composition is formulated as follows:

| Material | % w/w |
| --- | --- |
| Polymer A, B, C or D | 3.75 |
| Cyclopentasiloxane (99% active) | 0.15 |
| Benzophenone 4 | 0.0001 |
| Fragrance | 0.25 |
| Ethanol | 58.00 |
| Water | to 100% |

Example 8

The following is an example of a shampoo composition according to the invention:

| Ingredient Chemical Name | Active weight % |
| --- | --- |
| SLES 2EO | 14 |
| Cocoamidopropylbetaine | 2 |
| Guar hydroxypropyltrimonium chloride | 0.1 |
| Dimethiconol | 1 |
| Crosslinked polyacrylic acid | 0.4 |
| Polymer A, B, C or D | 1 |
| Mica + titanium dioxide | 0.2 |
| Sodium benzoate | 0.5 |
| Water | to 100 |

Example 9

The following is an example of a hair conditioning composition according to the invention:

| Ingredient | Trade name | Supplier | Function | % w/w |
| --- | --- | --- | --- | --- |
| Deionised water | | | solvent | q.s. to 100 |
| Polymer A, B, C or D | | | | 1 |
| Behenyl trimethyl ammonium chloride | Genamin KDM-P | Clairant | cationic surfactant | 1 |
| Behenyl alcohol | | | fatty alcohol | 5 |
| Silicone emulsion | DC2-1784 | Dow Corning | conditioning ingredient | 2 |
| Disodium EDTA | | | sequesterant | 0.1 |
| Methyl paraben | Nipagin | Nipa Lab | preservative | 0.2 |
| Perfume | | | fragrance | 0.5 |

Example 10

The following is a further example of a hair conditioning composition according to the invention containing the polymer of the invention as the sole conditioning agent:

| Ingredient | Trade name | Supplier | Function | % w/w |
|---|---|---|---|---|
| Deionised water | | | solvent | q.s. to 100 |
| Polymer D | | | | 1 |
| Behenyl trimethyl ammonium chloride | Genamin KDM-P | Clairant | cationic surfactant | 1 |
| Behenyl alcohol | | | fatty alcohol | 5 |
| Disodium EDTA | | | sequesterant | 0.1 |
| Methyl paraben | Nipagin | Nipa Lab | preservative | 0.2 |
| Perfume | | | fragrance | 0.5 |

Example 11

Solutions of polymers A-D were applied to hair in a mannequin head test at levels of 1-2% by weight of polymer. The treated hair was assessed by a panel of experienced assessors compared to treatments using Gafquat 755N at a level of 2% by weight.

The results for (a) shown were obtained by scoring –1 if the panellist preferred the left hand side (Control), 0 if they saw no difference and 1 if they preferred the right hand side (Prototype). In the results for (b) shown, there was no option for choosing no difference (no 0 option). The amounts from 12 panellists were then added together to give the final value. The amount that they deviate from 0 shows the preference for one side over the other with a positive value showing that the polymer of the invention was preferred and a negative value indicating that the control was preferred.

2% polymer A compared to 2% Gafquat 755N (protocol (a)

| Attributes | 2% Polymer A |
|---|---|
| root lift | 11 |
| overall volume | 2 |
| overall body | 0 |
| stickiest | –7 |
| natural movement | 5 |
| smoothest | 0 |
| stiffness of hair | –2 |
| ease of comb | 5 |
| greasy look | –10 |

1% polymer B, C, D, E compared to 2% Gafquat 755N (protocol (b)

| Attributes | Polymer B (1%) | Polymer C (1%) | Polymer D (1%) | Polymer E (1%) |
|---|---|---|---|---|
| root lift | 10 | 4 | 10 | 2 |
| overall volume | 2 | 8 | 10 | 8 |
| overall body | — | — | — | — |
| stickiest | –2 | –6 | –10 | –6 |
| natural movement | — | — | — | — |
| smoothest | — | — | — | — |
| stiffness of hair | –2 | –12 | –8 | –6 |
| ease of comb | 4 | 6 | 12 | 8 |
| greasy look | –6 | –8 | –8 | 0 |

The invention claimed is:

1. A hair treatment composition comprising: at least one polymer comprising at least two hydrogen-bonding moieties, which may be the same or different, covalently bonded to each other by at least one polymeric, oligomeric or monomeric linker, wherein said linker comprises a sufficient number of single covalent bonds to maintain flexibility of the linker and wherein each hydrogen bonding moiety has at least 3 groups capable of forming a hydrogen bond with the same moiety or a different moiety; and from 0.1 to 50% by weight of the total composition of a hair conditioning agent and/or a cosmetically acceptable surfactant; wherein said hydrogen bonding moieties independently have the general formula I, II or III

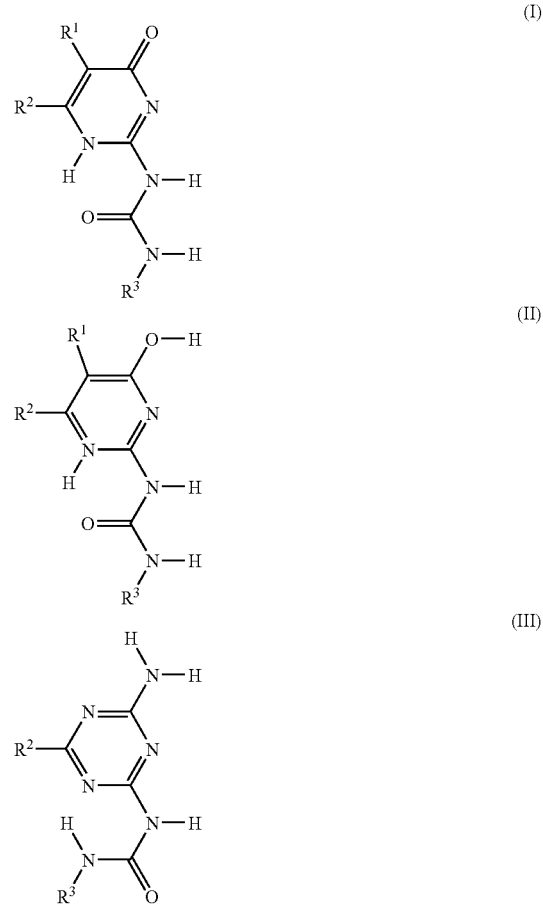

wherein $R^1$ is H, $C_1$-$C_{24}$ alkyl, $C_{2-24}$ alkenyl, $C_{2-24}$ alkynyl, aryl, aralkyl or heteroaryl groups, or polyoxyethylene or polyoxypropylene or a random or block copolymer thereof and $R^2$ and $R^3$ may be either a polymeric, oligomeric or monomeric linker or a side group selected from H, $C_1$-$C_{24}$ alkyl, $C_2$-$C_{24}$ alkenyl, $C_2$-$C_{24}$ alkynyl, aryl, aralkyl or heteroaryl groups, or polyoxyethylene or polyoxypropylene or a random or block copolymer thereof; wherein said alkyl, alkenyl, alkynyl, aryl, aralkyl or heteroaryl groups are optionally substituted with one or more amino, fluorine, chlorine, bromine, iodine, nitro, phenyl, hydroxyl, sulfide, thiol, ester or amide groups; and with the proviso that $R^2$ and $R^3$ are not both side groups;

wherein the hair treatment composition is a hair spray, mousse, tonic, gel, shampoo, conditioner or rinse.

2. A composition according to claim 1 wherein the polymeric, oligomeric or monomeric linker is selected from the group consisting of: polysiloxanes; polysilicones; polyethers; polyesters; polyamides; polyurethanes; polyureas; polyacrylates; polymethacrylates; polyacrylamides; polyvinylacetate; polyvinylalcohol; polyethylene; polybutylene; polybutadiene; and combinations thereof.

3. A composition according to claim 1 which comprises at least one polymer comprising two hydrogen-bonding moieties and at least one polymer comprising more than two hydrogen-bonding moieties.

4. A composition according to claim 1 which further comprises an additional hair styling polymer.

5. A composition according to claim 1, further comprising a cosmetically acceptable diluent or carrier comprising ethanol and/or water.

6. A composition as claimed in claim 5 in which the composition comprises at least 40% by weight water.

7. A composition according to claim 1 which is a hair spray or mousse.

8. A composition as claimed in claim 1 which is a shampoo or conditioner.

9. A method of treating hair comprising applying to the hair a hair treatment composition according to claim 1.

* * * * *